United States Patent [19]
McDonald

[11] Patent Number: 4,757,692
[45] Date of Patent: Jul. 19, 1988

[54] EMBRYO FREEZER

[76] Inventor: Gordon K. McDonald, 19790-88th Avenue, Langley, British Columbia, Canada, V3A 6Y3

[21] Appl. No.: 132,461

[22] Filed: Dec. 14, 1987

[51] Int. Cl.⁴ .............................................. E24F 3/16
[52] U.S. Cl. .......................................... 62/69; 62/78; 62/514 R
[58] Field of Search .................. 62/62, 68, 69, 70, 78, 62/514 R

[56] References Cited

U.S. PATENT DOCUMENTS

| | | | |
|---|---|---|---|
| 3,473,343 | 10/1969 | Chamberlain | 62/7 |
| 4,256,576 | 3/1981 | Blickle et al. | 62/70 |
| 4,306,425 | 12/1981 | Sitte et al. | 62/514 R |
| 4,388,814 | 6/1983 | Schilling | 62/514 R |
| 4,429,542 | 2/1984 | Sakao et al. | 62/78 |
| 4,455,842 | 6/1984 | Granlund | 62/78 |
| 4,459,823 | 7/1984 | Josephs et al. | 62/514 R |
| 4,459,825 | 7/1984 | Crouch | 62/78 |
| 4,485,641 | 12/1984 | Angelier et al. | 62/78 |
| 4,537,034 | 8/1985 | Crouch | 62/78 |

Primary Examiner—Ronald C. Capossela
Attorney, Agent, or Firm—Barrigar & Oyen

[57] ABSTRACT

An embryo freezer is disclosed in which the freezing chamber is mounted in the neck of a liquid nitrogen tank. The rate of cooling of the freezing chamber is regulated by adjusting the height of the freezing chamber within the neck of the liquid nitrogen tank. The embryo is stored in a straw which is in turn suspended in liquid methyl hydrate within the freezing chamber. Air is bubbled through the liquid in the freezing chamber to maintain a uniform temperature throughout the freezing chamber.

8 Claims, 3 Drawing Sheets

EMBRYO FREEZER

BACKGROUND OF THE INVENTION

The invention relates to the field of controlled rate freezers, and more particularly to the field of devices for freezing animal embryos.

It is currently practised in the area of breeding domestic livestock, such as cattle, to improve the genetic characteristics of a particular herd by obtaining an embryo from a high quality donor animal and transplanting the embryo to the uterus of a lower quality host animal which then gives birth to the higher quality young animal. This is a much less expensive way of obtaining the higher quality young animal than having the donor animal give birth to the young animal and then transporting the animal to the new herd.

In order to transport the embryo over any significant distance it is necessary to freeze the embryo and maintain it in frozen condition, typically stored in liquid nitrogen. The process of freezing the embryo is a delicate process due to the properties of living tissue. The rate at which the embryo is frozen is crucial. Cooling the embryo at too rapid a rate will result in the death of the embryo.

In the case of bovine embryos, a particular bovine embryo freezing curve has been found to be most effective. Starting at a temperature of approximately 20 degrees centigrade, the temperature of the embryo is allowed to drop guickly to about minus 5 degrees centigrade. The temperature of the embryo is held at that temperature for about five minutes while the solution containing the embryo is "seeded". This is the process of the induction of ice crystallization in the buffer solution in which the embryo is stored in the straw. Typically, it is a solution having about 10 percent qlycerol. Once the buffer solution is completely "seeded", the temperature of the embryo is dropped at a rate of about 0.5 degrees centigrade per minute to a temperature of between minus 30 degrees centigrade and minus 35 degrees centigrade. The embryo can then be plunged directly into liquid nitrogen ($-196°$ C.) for storage.

In the past, two general types of embryo freezers have been utilized. The first type has been a computer-controlled liquid nitrogen freezer. In this case, the embryo, stored in a straw or ampoule, is held in a temperature- controlled chamber. The temperature of the chamber is controlled by adjusting a flow of liquid nitrogen vapour to the chamber using a computer-controlled valve and also utilizing a heater in conjunction with the flow of liquid nitrogen. The computer is previously programmed with the proper freezing curve and the controller regulates the flow of liquid nitrogen and the heating action of the heater in order to follow the prescribed freezing curve. Such devices require relatively complicated electronic circuitry which makes the devices both expensive and bulky and subject to loss of calibration when transported. Also in some of these devices it is necessary to open the chamber at one point during each freezing operation. This can result in an unwanted rapid warming of the embryo and possible damage to the embryo.

A second common type of embryo freezer is a mechanical freon refrigeration device. In such devices, the standard freon mechanical refrigerator cools an alcohol "heat-sink" freezing chamber. The use of a heater in conjunction with the refrigerator allows the rate of temperature change to be regulated. This sort of device is preferable to the liquid nitrogen chamber in that the temperature of the embryo immersed in the alcohol heat-sink is less readily influenced by the opening and closing of the lid of the freezing chamber. However, again the device requires complicated electronic circuitry which makes it expensive, bulky, difficult to transport and difficult to maintain in calibration.

A recent improvement in such devices has been made by Dr. Peter Elsden. The lack of portability of the previous devices has been overcome by freezing the embryos in a simple solid metal cylinder which is suspended in the neck of a liquid nitrogen refrigerator tank. The solid metal cylinder is bored out to receive the straws. The height at which the cylinder is suspended in the neck determines the rate at which the metal core cools. The problem with the device, however, is the fact that there is a large temperature gradient between the top and bottom of the metal cylinder. For proper operation, all the embryos stored in the cylinder as well as the temperature sensing tip of the temperature probe must be suspended at exactly the same height within the metal cylinder. This requires considerable care when placing the embryos within their straws. Also, there will be an air space between the straw and the supporting metal of the freezing chamber and this makes the heat transfer which occurs within the freezing chamber less efficient than if the straw were immersed in a "heat-sink" liquid such as alcohol.

SUMMARY OF THE INVENTION

The present invention provides a portable and inexpensive embryo freezer which does not require complicated electronic circuitry and yet which allows the freezing of the embryo to be accurately and readily regulated. The invention provides a freezing chamber which is adapted to be suspended in the neck of a liquid nitroqen tank and whose height within the neck of the tank may be regulated. The embryo-containing straws are mounted within the freezing chamber and are immersed in a liquid having a low freezing point such a alcohol. Air is constantly bubbled through the freezing chamber to maintain uniform temperature throughout the freezing chamber.

BRIEF DESCRIPTION OF THE DRAWINGS

In drawings which illustrate an embodiment of the invention.

DETAILED DESCRIPTION OF A PREFERRED EMBODIMENT OF THE INVENTION

Figure 1:
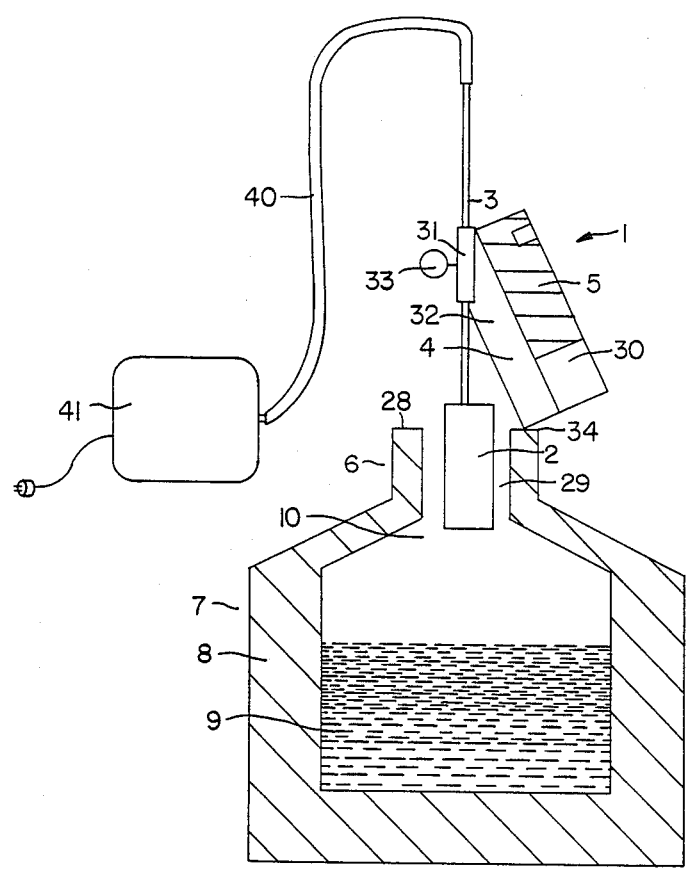
FIG. 1 is a cross-sectional view of the liquid nitrogen tank showing the embryo freezer of the invention suspended in the neck of the tank.

Referring to FIG. 1, the embryo freezer of the invention is designated generally as 1. It consists of a freezing chamber 2, chamber support rod 3, thermometer support 4 and digital thermometer 5. Freezing chamber 2 is suspended within the neck 6 of liquid nitrogen tank 7. Tank 7 has thick insulated walls 8 and contains a guantity of liquid nitrogen 9. Area 10 of the tank is filled with gaseous nitrogen which has evaporated from the liquid and is at a low temperature.

Figure 2:
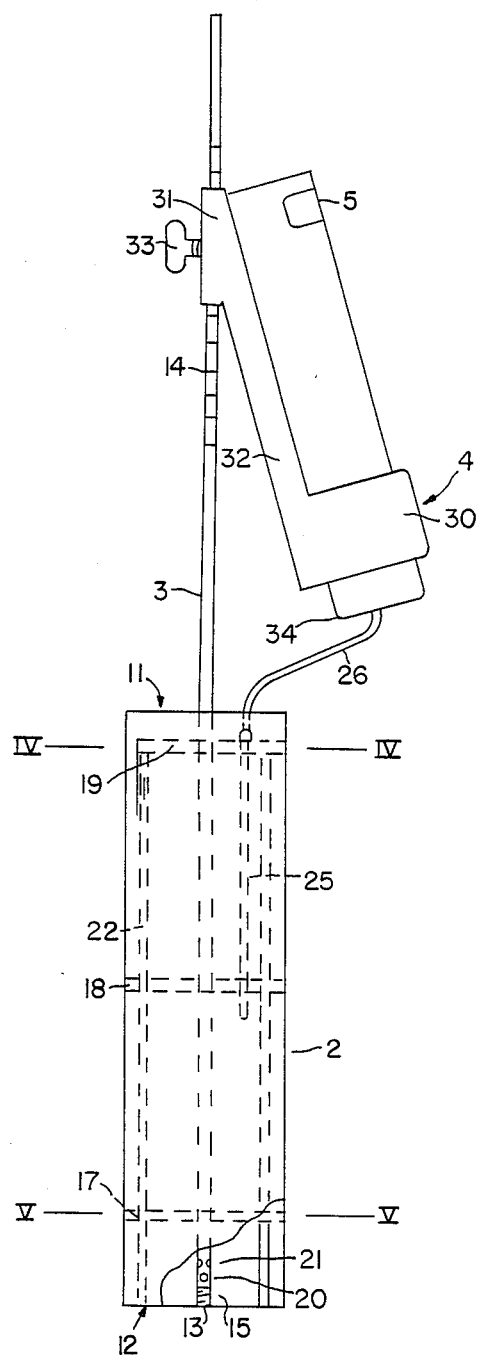
FIG. 2 is an elevational view of the embryo freezer of the invention showing the interior of the freezing chamber in phantom outline and with the freezing chamber partially cut-away.

Referring to FIG. 2, the freezing chamber 2 is a hollow aluminum cylinder 140 millimeters in length, 38.1 millimeters in diameter with a wall thickness of 1.2 millimeters. The upper end 11 of the freezing chamber is open, and the lower end 12 is closed to allow the chamber to hold a liquid.

The chamber support rod 3 is a hollow aluminum tube with an outside diameter of 5 millimeters and a wall of 0.8 millimeters. The upper portion of the tube has regular graduations 14 marked on the exterior surface for positioning of the thermometer. The support tube may be separated into two sections joined by a screw fitting to allow the tube to be broken down in to two sections for easier transport. The bottom end 15 of the tube is threaded to receive threaded bolt 13 which is soldered or welded to the bottom of freezing chamber 2. Two holes 20 and 21 are drilled through the lower end of the tube as shown in FIG. 2 to allow air to escape from the center of the tube. Three support rods 22 are soldered at points of penetration through tube sheets 17, 18 and 19. These rods stand on the bottom 12 of chamber 2 and serve to support tube sheets 17, 18 and 19 which in turn are perforated to form a rack for the straws and temperature probe. This straw rack can slide freely up and down in the freezing chamber 2 on rod 3, but normally rests on the freezing chamber floor 12.

Figure 4:
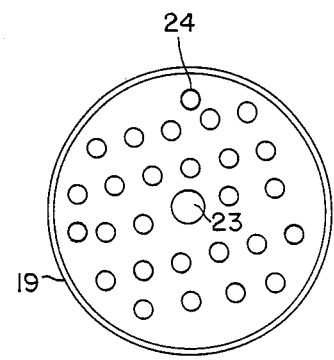
FIG. 4 is a cross-sectional view taken along line IV—IV of FIG. 2.
Figure 5:
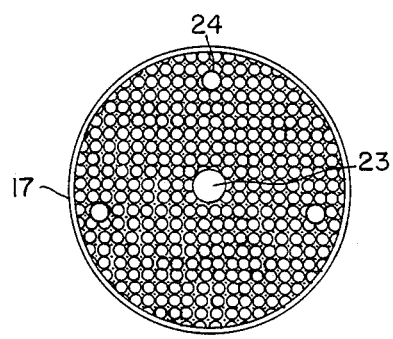
FIG. 5 is a cross-sectional view taken along line V—V of FIG. 2.

Tube sheets 18 and 19 are as shown in FIG. 4, and in addition to having a central hole 23 for receiving support rod 3 and three holes 24 for receiving rods 22, will have an array of holes for receiving the embryo-carrying straws. In the case of the embryo straws, the holes will be three millimeters in diameter. For controlled freezing of other sorts, these holes can be made larger or smaller to receive different-sized vials. Tube sheet 17, shown in FIG. 5, is a fine mesh designed to support the straws and act as a diffuser for the air bubbles.

Digital thermometer 5 is a thermometer with a constant digital read-out of the temperature of its probe 25. For example, a suitable thermometer would be that sold under the trade mark KM200. Such a thermometer is battery-operated. The probe 25 is appropriately sized to sit in the array of holes in the straw rack. The probe is connected to the thermometer by an electrical connection 26.

The thermometer holder 4 consists of a bracket 30 into which the thermometer slides and is held, a bracket 31 which slides on the support rod 3, a plate 32 connecting brackets 31 and 30, and a thumb-screw 33 for tightening bracket 31 into a given position on the support rod. Plate 32 has a lower surface 34 which is positioned to rest on the upper edge of the neck of liquid nitrogen container 7.

An air tube 40 is connected to the upper end of hollow tube 3 and the other end of tube 40 is connected to an air bubbler 41 which is electrically operated to pump air bubbles through air hose 40. A suitable device is an air pump model No. MH7776 manufactured by Man Hing Electrical Manufactory as an aquarium air-pump.

To utilize the device, the freezing chamber is filled with methyl-hydrate to a level approximately level with the top of the straw rack plate 19 prior to assembling in the neck of a liquid nitrogen tank. The embryo freezer is assembled as shown in FIG. 1 with surface 34 of thermometer holder 30 resting on the upper edge 28 of the nitrogen tank 7. Thumb screw 33 is tightened to hold the support rod and the supported freezing chamber at the appropriate height within the neck of the tank. There will be a slight air space 29 between the freezing chamber and the neck of the tank which will be filled with escaping low-temperature gaseous nitrogen. The digital thermometer is activated and the temperature probe inserted in the straw rack.

The air bubbler 41 is plugged in and thereby activated. This causes air to bubble up from holes 20 and 21 in the support rod through the diffusing sheet 17 and then up through the freezing chamber.

The thermometer holder in this way regulates the level at which the freezing chamber sits within the neck of the nitrogen tank. Lowering the freezing chamber by releasing thumb screw 33 and moving bracket 31 farther up on the graduated chamber rod will cause the freezing chamber to be inserted more deeply into the nitrogen tank and result in a more rapid rate of cooling. The rate at which the freezing chamber cools is determined by monitoring the digital thermometer and utilizing a watch or clock to determine the rate of cooling.

Figure 3:
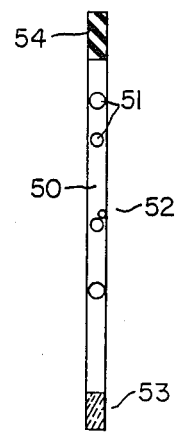
FIG. 3 is a cross-sectional view of an embryo straw.

The embryos are loaded in the $\frac{1}{4}$ cubic centimeter straws as shown in FIG. 3. Such straws are sealed with a factory plug at one end. The embryo in a buffer solution of approximately 10 percent glycerol is loaded into the straw and the end of the straw is sealed with polyvinylchloride powder. Typically there will be a number of air bubbles 51 placed in straw 50 in order to trap the embryo in the centre of the straw. The embryo is designated as 52, the PVC plug is 53 and the factory plug is 54.

The embryo-containing straw is inserted into the straw-rack 56 (consisting of tube sheets 17, 18 and 19) joined by support rods 22. The height of the freezing chamber will have been pre-set to the appropriate height, although the temperature will be continuously monitored and the height of the freezing chamber may be changed. In this way the temperature in the chamber is allowed to guickly drop to approximately minus 4 degrees centigrade. The height of the chamber is then raised to the next level so that the temperature decline decreases. The temperature of the freezing chamber is then held at the temperature of minus 5 degrees centigrade and the seeding process is commenced by touching the top of the column of buffer solution in which the embryo sits with liquid nitrogen-cooled forceps. The temperature of the freezing chamber is then held at minus 5 degrees centigrade for approximately 5 minutes or until the ice crystals fill the entire embryo column 50. At this point the freezing chamber is again lowered more deeply into the neck of the tank and the temperature is dropped at a rate of 0.5 degrees centigrade per minute to a temperature of between minus 30 and minus 35 degrees centigrade. The frozen embryo is then removed from the freezing chamber and it is plunged directly into liquid nitrogen.

The bubbling of air through the methyl hydrate liquid causes the temperature of the methyl hydrate in the freezing chamber to be generally uniform from top to bottom. Also, the bubbling of air though the methyl hydrate causes the rate of temperature drop of the liquid to be more linear than would otherwise be the case. As the liquid becomes colder, normally the rate at which it cools decreases. However, the bubbling of warm (room temperature) air through the methyl hydrate causes the cooling rate to be slower in the initial stages than would normally be the case. As the liquid becomes colder, it becomes more viscous and the rate of bubbling through the liquid becomes slower and thus the effect of the heat distributing bubbling on the rate of cooling of liquid decreases the colder the liquid gets. The result is that the methyl hydrate cools in a more linear manner than would otherwise be the case which is advantageous in the present application.

While various alterations and modifications of the structure and method above-described will be apparent to those skilled in the art without departing from the spirit of the invention, the scope of the invention is to be construed in terms of the accompanying claims.

THE EMBODIMENTS OF THE INVENTION IN WHICH AN EXCLUSIVE PROPERTY OR PRIVILEGE IS CLAIMED ARE DEFINED AS FOLLOWS:

1. A device for freezing objects at a controlled rate comprising:
   (a) an insulated tank for containing an extremely cold liquid;
   (b) a chamber for holding the objects to be frozen and adapted to be mounted in the neck of said tank and containing a liquid having a low freezing point;
   (c) means for regulating the height of said freezing chamber in the neck of said tank; and
   (d) means for bubbling gas through the liquid stored in said freezing chamber.

2. A method of freezing objects at a controlled rate comprising the steps of:
   (a) providing a tank of liquid nitrogen or similar cold liquid having a constricted neck;
   (b) providing a freezing chamber filled with a liquid having a low freezing point such as methyl hydrate;
   (c) placing the object to the frozen in said freezing chamber and regulating the height of said freezing chamber within the neck of said tank; and
   (d) bubbling gas from the bottom of the freezing chamber up through said liquid.

3. The device of claim 1 wherein said gas is air.

4. The device of claim 1 wherein said freezing chamber further comprises apparatus for holding said objects.

5. The device of claim 1 further comprising a thermometer.

6. The device of claim 1 wherein said means for regulating comprises a support rod on which said freezing chamber may be secured at various locations.

7. The device of claim 6 wherein said regulating means further comprises support means slidably received on said support rod and having a surface adapted to bear against said neck of said tank.

8. The device of claim 6 wherein said support rod is hollow and provided with apertures at the lower end thereof to provide said gas bubbles in said freezing chamber.

* * * * *

UNITED STATES PATENT AND TRADEMARK OFFICE
CERTIFICATE OF CORRECTION

PATENT NO. : 4,757,692
DATED : July 19, 1988
INVENTOR(S) : Gordon K. McDonald

It is certified that error appears in the above-identified patent and that said Letters Patent are hereby corrected as shown below:

Column 1, line 30, change "guickly" to --quickly--.

Column 1, line 36, change "qlycerol" to --glycerol--.

Column 2, line 38, change "nitroqen" to --nitrogen--.

Column 3, lines 2 to 3, change "guantity" to --quantity--.

Column 4, line 41, change "guickly" to --quickly--.

Column 6, line 8, "to the frozen" should read --to be frozen--.

Signed and Sealed this

Twenty-eighth Day of February, 1989

Attest:

DONALD J. QUIGG

Attesting Officer     Commissioner of Patents and Trademarks